US012653481B2

(12) United States Patent
Brueck et al.

(10) Patent No.: US 12,653,481 B2
(45) Date of Patent: Jun. 16, 2026

(54) METHOD FOR PROVIDING GUIDANCE DATA IN AN X-RAY SYSTEM

(71) Applicant: KONINKLIJKE PHILIPS N.V., Eindhoven (NL)

(72) Inventors: Heiner Matthias Brueck, Pinneberg (DE); Daniel Bystrov, Hamburg (DE); Sven Krönke, Hamburg (DE); André Goosen, Eldena (DE); Jens Von Berg, Hamburg (DE); Stewart Matthew Young, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 164 days.

(21) Appl. No.: 18/683,821

(22) PCT Filed: Aug. 8, 2022

(86) PCT No.: PCT/EP2022/072188
§ 371 (c)(1),
(2) Date: Feb. 15, 2024

(87) PCT Pub. No.: WO2023/020865
PCT Pub. Date: Feb. 23, 2023

(65) Prior Publication Data
US 2024/0366173 A1 Nov. 7, 2024

(30) Foreign Application Priority Data
Aug. 17, 2021 (EP) ..................................... 21191761

(51) Int. Cl.
*A61B 6/00* (2024.01)

(52) U.S. Cl.
CPC ............ *A61B 6/541* (2013.01); *A61B 6/5211* (2013.01)

(58) Field of Classification Search
None
See application file for complete search history.

(56) References Cited

U.S. PATENT DOCUMENTS

| | | | |
|---|---|---|---|
| 7,837,621 B2 | 11/2010 | Kruase | |
| 2004/0068187 A1 | 4/2004 | Krause | |
| 2016/0074004 A1* | 3/2016 | Braun ..................... | G06F 3/017 |
| | | | 378/205 |
| 2016/0213329 A1 | 7/2016 | Dirkes | |

(Continued)

OTHER PUBLICATIONS

PCT International Search Report, International application No. PCT/EP2022/072188, Dec. 12, 2022.

(Continued)

*Primary Examiner* — Hoon K Song
(74) *Attorney, Agent, or Firm* — Larry Liberchuk

(57) ABSTRACT

The invention is related to a method for providing guidance data (30, 41) for positioning a region of interest (20, 31, 41, 56) of a subject (54), an X-ray source (52), and an X-ray detector (21, 34, 53). The method comprises: obtaining, by a processor (11), current positioning data of at least one palpable bony landmark (23, 33) derived from a palpation; obtaining current positioning data of the X-ray source (52) and of the X-ray detector (21, 34, 53) (S20); determining guidance data (30, 41) for positioning the region of interest (20, 31, 41, 56), the X-ray source (52) and the X-ray detector (21, 34, 53) and providing, by the processor (11), the guidance data (30, 41) (S40).

12 Claims, 3 Drawing Sheets

(56) References Cited

U.S. PATENT DOCUMENTS

| | | | |
|---|---|---|---|
| 2017/0100089 A1 | 4/2017 | Chang | |
| 2018/0116613 A1 | 5/2018 | Von Berg | |
| 2019/0183439 A1* | 6/2019 | Joerger | A61B 6/545 |
| 2020/0375546 A1* | 12/2020 | Shoudy | A61B 6/04 |
| 2021/0158028 A1 | 5/2021 | Wu | |
| 2021/0158107 A1 | 5/2021 | Karanam | |
| 2021/0158937 A1 | 5/2021 | Wu | |
| 2023/0375546 A1 | 11/2023 | Qin | |

OTHER PUBLICATIONS

Cao Z. et al., Realtime Multi-Person 2D Pose Estimation Using Part Affinity Fields, 2017 IEEE Conference on Computer Vision and Pattern Recognition (CVPR), Honolulu, HI, pp. 1302-1310, 2017.
Nakano N. et al., "Evaluation of 3D Markerless Motion Capture Accuracy Using OpenPose with Multiple Video Cameras", Frontiers in Sports and Active Living, vol. 2, article 50, May 2020.
Clever H.M. et al., "3D Human Pose Estimation on a Configurable Bed from a Pressure Image", 2018 IEEE/RSJ International Conference on Intelligent Robots and Systems (IROS), Madrid, pp. 54-61, Oct. 2018.
Sorriento A. et al., "Optical and Electromagnetic Tracking Systems for Biomedical Applications: A Critical Review on Potentialities and Limitations.", IEEE Rev Biomedical Engineering, vol. 13, pp. 212-232, 2020.
Parizi F.S. et al., "AuraRing: Precise Electromagnetic Finger Tracking", Proceedings of the ACM on Interactive, Mobile, Wearable and Ubiquitous Technologies, vol. 3, No. 4, Article No. 150, pp. 1-28, Dec. 2019.
Park J. et al., "A Finger Grip Force Sensor with an Open-Pad Structure for Glove-Type Assistive Devices", Sensors (Basel), vol. 20, No. 4, pp. 1-15, Dec. 2019.
Janbaz et al., "Programmable Soft Actuators Show in the Great Potential of Soft Robotics", Delft University of Technology, Jul. 2019. https://phys.org/news/2019-07-programmable-soft-actuators-great-potential.html.
Evarts H. et al., "A Tactile Robot Finger with No. Blind Spots", Photo and Video Credit: Pedro Piacenza Columbia Engineering, Feb. 26, 2020. https://www.engineering.columbia.edu/press-releases/ciocarlie-tactile-robot-finger.
TactileGlove—Hand Pressure And Force Measurement, downloaded from the Internet Feb. 8, 2024. https://pressureprofile.com/body-pressure-mapping/tactile-glove.

* cited by examiner

METHOD FOR PROVIDING GUIDANCE DATA IN AN X-RAY SYSTEM

FIELD OF THE INVENTION

The invention relates to a method for providing guidance data for positioning a region of interest of a subject, an X-ray source and an X-ray detector, to a device for providing guidance data for positioning a region of interest of a subject, an X-ray source, and an X-ray detector, to a system for medical imaging, and to a computer program element.

BACKGROUND OF THE INVENTION

In medical imaging. X-ray imaging is a widely used medical imaging method. X-ray systems are state of the art and therefore known. The quality of the medical image obtained by such an X-ray system depends among others on a quality of a preparation of the medical imaging process preceding the actual image acquisition, in particular on an alignment of a subject to the X-ray system. In case the quality of a medical image is insufficient, medical imaging has to be repeated or even worse, a wrong medical diagnosis may be derived from the medical image. In sum, this may lead to increased costs for medical imaging, wrong medical diagnosis, higher radiation exposure, and to a reduced image quality.

US 2016/0074004 A1 describes positioning of an examination table relative to a medical-technical imaging installation. Thereby, a camera aligned with an examination table; and a display and operating unit, designed for outputting a camera image, includes a microprocessor. The microprocessor configured to cause the apparatus to freeze the camera image on the display and operating unit in a manner temporally dependent on a first user interaction, and define reference location information on the examination table in the frozen camera image on the basis of a second user interaction; and move the examination table or the medical-technical imaging installation with the aid of a positioning system, wherein the reference location information is brought to congruence with a recording region of the medical-technical imaging installation.

US 2020/0375546 A1 describes a medical imaging guidance system that comprises a patient sensor configured to receive three-dimensional (3D) data associated with a patient, an imaging system comprising an imaging hardware component configured to acquire image data of an anatomical feature associated with the patient, wherein the imaging system comprises a hardware position sensor associated with the imaging hardware component; and a processor configured to generate a 3D surface map associated with the patient based on the 3D data: generate a 3D patient space from the 3D surface map associated with the patient: generate a 3D patient model by mapping an anatomical atlas to the 3D patient space, wherein the 3D patient model comprises one or more 3D representations of anatomical features of a human body within the 3D patient space: determine a desired position associated with the imaging hardware component to acquire image data of the anatomical feature: determine a current position associated with the imaging hardware component from the hardware position sensor; and determine a desired movement associated with the imaging hardware component to position the imaging hardware component at the desired position.

SUMMARY OF THE INVENTION

There may, therefore, be a need for providing guidance data in X-ray imaging, in particular in the preparation phase of X-ray imaging. The object of the present invention is solved by the subject matter of the independent claims, wherein further embodiments are incorporated in the dependent claims.

According to a first aspect, a method for providing guidance data for positioning a region of interest of a subject, an X-ray source, and an X-ray detector is provided. The method comprises the steps of: Obtaining, by a processor, current positioning data of at least one palpable bony landmark of the region of interest from a measuring device, wherein the current positioning data is derived from a palpation of the at least one palpable bony landmark. Obtaining, by the processor, current positioning data of the X-ray source and of the X-ray detector. Determining, by the processor, guidance data for positioning the region of interest, the X-ray source and the X-ray detector by utilizing a parametric 3D model, configured to describe a pose of the region of interest, and the obtained current positioning data of the at least one palpable bony landmark, of the X-ray source, and of the X-ray detector. Providing, by the processor, the guidance data.

The term guidance data, as used herein, is to be understood broadly and relates to any information configured to guide an adaption of an alignment of a region of interest, an X-ray source and an X-ray detector from a current alignment to a desired alignment. The guidance data may comprise positioning data such as translational and rotational degrees of freedom of the region of interest, the X-ray source and the X-ray detector. The guidance data may comprise degrees of freedom from a joint of the region interest (e.g. knee joint). The guidance may data may comprise shift values from a current alignment to a desired alignment (e.g. shift x-position of the X-ray detector 100 mm in x-direction or shift knee joint angle −5)°. The guidance data may presented by means of visual signals (e.g. display) or audio signals (e.g. loud speaker announcements). The guidance data may be intended for medical personnel, such as a radiographer who operates, monitors, or the like the imaging system. The guidance data may be intended as control information for an imaging system, wherein the guidance data is configured to control the imaging system to position automatically the X-ray source and the X-ray detector. Further, the imaging process itself may, optionally, be performed at least semi-automatically.

The term subject, as used herein, is to be understood broadly and relates to any human or animal.

The term region of interest, as used herein, is to be understood broadly and relates to any part of the subject. For example, the region of interest may be a bone, a joint, a hip, a bone arrangement of two or more bones and one or more joints (e.g, ankle joint with lower leg bones und foot bones). The region of interest may also comprise the entire subject itself.

The X-ray source and X-ray detector, as used herein, are to be understood as main elements of an X-ray system. The X-ray source and X-ray detector may be positioned independently from each other. The position of the X-ray source and X-ray detector may be known by a control of the X-ray system. The position of the X-ray source and the X-ray detector may be measured by a measuring device such as a range camera or a laser interferometer. The X-ray detector may in the form of digital cassette detector, which can be placed without limitation in the field of view of the X-ray source. For example, the position of the X-ray source and/or the X-ray detector can be determined and/or indicated absolutely, e.g. by absolute coordinates in a correspondingly defined coordinate system, and/or relative, e.g, to a generally defined reference point or to each other.

The term palpable bony landmark, as used herein, is to be understood broadly and relates to a bony landmark, which is normally hidden by tissue and skin of a subject such that the palpable bony landmark cannot be detected directly, i.e. it cannot be seen, by e.g, a visual system (e.g. human eyes or a camera) or the like. The palpable bony landmark may be a suitable bone part, bone section, etc., such as a foot ankle, which might be hidden by too much tissue of an overweight person. However, a radiographer nevertheless may palpate the foot ankle.

The term processor, as used herein, is to be understood broadly and relates to any electronic data processing unit configured to carry out the steps of a method described above. The processor may be implemented in hardware and/or software. The processor may be a single entity or distributed on a plurality of entities.

The term positioning data, as used herein, relates to any spatial information configured to describe a position or an alignment of a region of interest, an X-ray source, and an X-ray detector. The positioning data may comprise absolute values and relative values in a coordinate system (e.g. coordinate system of an X-ray imaging system or a coordinate system of the region of interest or a subject). The term current, as used herein, means the positioning data existing now.

The term measuring device, as used herein, is to be understood broadly and relates to any sensor or sensor arrangement, i.e. one or more sensors, configured to determine a position. The measuring device may comprise one or more of the following: RGB camera, RGB-D camera, range camera, laser interferometer, wherein this is not limited herein. The measuring device may be arranged to be directed towards the region of interest, e.g, above the region of interest or lateral of the region of interest. The measuring device may be in a wired (e.g, a communications network, such as Ethernet, etc.) or wireless (e.g. WIFI) connection with the processor.

The term palpation, as used herein, is to be understood broadly and relates to a tactile sampling. The palpation may comprise a palpation carried out by a human (e.g, a radiographer) or by a soft tissue robot. Palpation may also be carried out by a human with an auxiliary instrument, such as a pointing device or the like.

The term parametric 3D model, as used herein, is to be understood broadly and relates to a model configured to describe a geometric alignment between a region of interest, an X-ray source, and X-ray detector. The parametric 3D model may further be configured to describe the region of interest by means of parameter indicative for dimensions or sizes of parts (e.g. bones) of the region of interest and one or more degrees of freedom of the region of interest (e.g. flexion angle of the knee joint). The parametric 3D model is further configured to describe a pose of the region of interest. i.e, a spatial position of the region of interest, which pose or spatial position may also be referred to as the combination of position and orientation of a rigid body, such as the subject's body or the region of interest. In other words, the parametric 3D model describes the imaging alignment in general and in particular one or more dimensions or sizes and one or more degrees of freedom of the region of interest. The parametric 3D model may, for example, get measured positioning data as input and may output a current alignment of the region of interest, the X-ray source, and the X-ray detector. The current alignment may be described with positioning data of one or more elements of region of interest, of the X-ray source and the X-ray detector.

The invention is based on the finding that the quality of a medical image is crucial for follow-up diagnosis of the medical image. The quality of the medical image depends on what the medical image should show. E.g, a special gap between two bones in a special perspective, e.g, a gap between medial malleolus and lateral malleolus in a special direction of the radiation beam. In other words, the quality of the medical image acquired depends on an angle between a central beam of the X-ray imaging system and e.g, a joint axis of a knee of a patient, wherein the knee is the region of interest. The desired angle may be derived from guidelines for generating radiographs or the like. To obtain such a medical image with a desired angle between the central beam and the joint, the region of interest, the X-ray source and the X-ray detector have to be aligned accordingly. As the region of interest (e.g, a gap between medial malleolus and lateral malleolus or a knee joint) is hidden by tissue and skin of the subject (i.e. patient), it is sometimes not clear how the region of interest, the X-ray source, and the X-ray detector have to be positioned. In clinical practice, radiographers with a lot of experience feel palpable bony landmarks or palpable bony prominences and put the haptic impression in a 3-dimensional context in order to position the region of interest, the X-ray source and the X-ray detector. However, this requires a huge experience of the radiographer. The invention proposes to simplify this approach by detection of the current positioning data of the at least one palpable bony landmark, the X-ray source and the X-ray detector and to provide to a radiographer guidance data based on the current positioning data how to position the region of interest, the X-ray source, and the X-ray detector. In other words, the invention assists the radiographer computer-aided in preparing the alignment of the region of interest, the X-ray source, the X-ray detector such that no highly experienced radiographer is necessary. This may be advantageous as it simplifies the imaging process, in particular the preparation phase. This may be advantageous in terms of quality, cost, and efficiency. This may be advantageous as no radiographer with huge experience is required for the imaging process. A key benefit may be that less experienced radiographers can easily adapt the positioning without using radiation (i.e. low-dose pre-image or retake). The positioning and/or aligning of the region of interest, the X-ray source and the X-ray detector may be advantageously carried before X-ray imaging process. This may further be advantageous to train unexperienced radiographers. A further benefit may be that the method does not require marker or the like.

According to an embodiment, the obtaining the current positioning data of the at least one palpable bony landmark may comprise measuring a spatial position of at least a fingertip of a radiographer or a soft tissue palpation robot palpating the at least one palpable bony landmark. The measured spatial position may be registered to a coordinate system (e.g. coordinate system of the X-ray system). The underlying registering algorithm may involve a weighting in dependency of expected accuracy of the measured positioning data. E.g., a radiographer palpates the region of interest (e.g, an ankle joint) and detects with one fingertip of his left hand the lateral malleolus (i.e. first palpable bony landmark) and with one fingertip of his right hand the medial malleolus (i.e. second palpable bony landmark). The position of the visible fingertip indirectly reveals the position of the invisible palpable bony landmark. By measuring the spatial position of the fingertip, the spatial position of the palpable bony landmark can be easily determined. In case a radiographer palpates the region of interest, a measuring device such as range camera, one or more cameras may measure the spatial position. Alternatively, the radiographer may utilize an auxiliary instrument. e.g. may wear a tracking device on his hand, or his wrist, or on his finger (e.g, an electromagnetic tracking device or reflective markers for optical tracking). In case, a soft tissue robot palpates the region of interest, the positioning data of the palpable bony landmark is determined by a control of the soft tissue robot, which tracks the continuously the spatial position of extremities of the soft tissue robot. The soft tissue robot may be equipped with a touch sensor to perform the palpation and/or the patient positioning. This may be advantageous as the position to the at least one palpable bony landmark is determined accurately. The radiographer may be equipped with a touch sensor (e.g. gloves with a touch sensor on the fingertip).

According to an embodiment, obtaining the current positioning data of the at least one palpable bony landmark may comprise a trigger signal configured to indicate that at least one fingertip of a radiographer or a soft tissue palpation robot palpates the at least one palpably bony landmark. By means of the trigger signal a synchronization of the palpation of the at least one bony landmark and the obtaining of the positioning data thereof can advantageously be achieved. The trigger signal may be received by a measuring device (e.g. microphone, button, camera, pressure sensor or touch sensor) and may be transmitted to the processor in order to start the measuring of the spatial position of the at least one palpable bony landmark. This may be advantageous in terms of accuracy and efficiency as it simplifies the process. This may be advantageous as the moment when a radiographer finds the palpable bony landmark is not otherwise observable.

According to an embodiment, the trigger signal may be generated actively by the radiographer and/or passively by a touch sensor arranged at the at least one fingertip of the radiographer or the soft tissue palpation robot. Examples for actively generating the trigger signal may comprise pressing a button, speech recognition, eye tracking, and gesture detection. For example, the radiographer may touch the at least one palpable bony landmark and then touch with the other hand a button in order to generate the trigger signal. For example, the radiographer may touch the at least one palpable bony landmark and then instruct the device verbally. e.g. by voicing "measure now" or the like, in order to generate the trigger signal, which instruction may be obtained by a microphone. For example, the radiographer may touch the at least one palpable bony landmark and then blink twice with his eyes in order to generate the trigger signal, which may be obtained by a camera. For example, the radiographer may touch the at least one palpable bony landmark and then raise the other hand in order to generate the trigger signal, which may be obtained by a camera. The touch sensor may detect an increased pressure indicative of the at least one palpable bony landmark. For example, the radiographer or the soft palpation robot may palpate the at least one palpable bony landmark, the radiographer or the soft palpation robot may increase the palpation pressure in order to generate the trigger signal. A post processing unit, for example, may process the pressure pattern and detect a trigger signal and transmit it to the processor in order to start the measuring of the spatial position of the at least one palpable bony landmark. This may further improve accuracy, efficiency, and flexibility.

In an embodiment, the determining the guidance data may comprise determining a pose of the region of interest by utilizing the parametric 3D model and the obtained current positioning data of the at least one palpable bony landmark of the region of interest. The term pose, as used herein, relates to a spatial alignment of one or more elements (e.g. bones and joints) of the region of interest. The parametric 3D model may, for example, estimate a pose of the region of interest in dependency of the at least one palpable bony landmark. By determining the pose of the region of interest, an alignment within the region of interest may be advantageously determined. This may advantageously increase the accuracy of the guidance data. The parametric 3D model may further use, for example, for determining the pose of the region of interest one or more visible anatomical landmarks of the region of interest measured by a measuring device. This may increase the accuracy of the guidance data.

In an embodiment, the guidance data may comprise a comparison of the pose of the region of interest, the positioning data of the region of interest, the positioning data of the X-ray source and the X-ray detector with a target alignment of the region of interest, the X-ray source and the X-ray detector. The term target alignment of the region of interest, the X-ray source and the X-ray detector, as used herein, relates to an alignment derived from guidelines for imaging the respective region of interest or from an input of a specialist. The target alignment is described by positioning data of the region of interest, the X-ray source and the X-ray detector. The target alignment may be stored in a table or the like on a storage medium, which is in communication with the processor. The comparison may comprise a calculation of a difference between the positioning data of a current alignment and the target alignment, which may be advantageously processed into guidance data provided to a radiographer.

In an embodiment, the parametric 3D model may comprise one or more anatomical parameters of the region of interest, and wherein the anatomical parameters may comprise at least one scale parameter of the region of interest and at least one degree of freedom of a movement of the region of interest. The scale parameter may be a length, a surface, a volume of an element (e.g, a bone) of the region interest. The degree of freedom of a movement may be a displacement of an element (e.g, a bone) of the region of interest. The degree of freedom of a movement may be an angle of a joint (e.g. knee joint) of the region of interest. The degree of freedom of a movement may be a torsion of the region of interest or of an element of the region of interest. The parametric 3D model may be a generic model, which may be adapted in dependency of a subject or a region of interest to be imaged. For example, a scale parameter such as a length of a bone is different for a child and an adult. The scale parameter may adapted based on obtained anatomical landmarks of the region of interest. The parametric 3D model may be an articulated model. In other words, the parametric 3D model may relate to an adaptable multibody model, wherein the respective single bodies and the respective degrees of freedom of a movement may be advantageously adjusted to describe the reality as accurate as possible.

In an embodiment, the method may further comprise the steps of receiving, by the processor, current positioning data of one or more anatomical landmarks of the region of interest, from the measuring device: updating, by the processor, the parametric 3D model based on the received current positioning data of the one more anatomical landmarks of the region of interest. The term anatomical landmark, as used herein, relates to visible landmarks configured to be measured by a measuring device. The measuring device may be optical measuring device such as an RGB camera, a range camera, a RBG-D camera. In contrast to the palpable bony landmark, the anatomical landmark is visible and not hidden by tissue and/or skin. The measured anatomical landmarks may be used to update the 3D parametric model. E.g., the positioning data of two anatomical landmarks may be measured by a range camera, wherein the two anatomical landmarks are indicative for a length of the tibia. The parametric 3D model then may use measured information to update the parametric 3D model of the lower leg (i.e. region of interest in the present example). This may be advantageous as it increases the accuracy of the parametric 3D model and therefor of the guidance data. The measured spatial position of the anatomical landmarks may be registered to a coordinate system (e.g. coordinate system of the X-ray system or the region of interest). The underlying registering algorithm may involve a weighting in dependency of expected accuracy of the measured positioning data. This may be advantageous in terms of outliers.

In an embodiment, the measuring device may be an optical measuring device, in particular a range camera. The optical measuring may be a stereo-camera system, comprising two or more cameras. The optical measuring device may be arranged above or lateral the region of interest, the X-ray source, and/or the X-ray detector. The optical measuring device may be in a wired or a wireless communication with the processor. The optical measuring device may comprise one or more measuring sensors. The optical measuring device may be a single entity or distributed on a plurality of entities. The optical measuring device may comprise a communication interface.

According to an embodiment, the guidance data may be continuously determined and provided during positioning the region of interest of a subject, the X-ray source, and the X-ray detector. In other words, the method is carried out permanently during the preparation phase and therefor advantageously aids e.g. the radiographer. This may increase the efficiency and the quality of medical imaging. This is achieved by continuously executing the process steps of the method.

In an embodiment, providing the guidance data may comprise a visual representation; and/or an audio representation. The visual representation may be a display showing a schematic representation of the current alignment of the region of interest, the X-ray source and the X-ray detector and the target alignment. The visual representation may be shown in virtual-reality glasses or in augmented-reality glasses. The audio representation may be provided with loudspeaker or earphones to a radiographer, wherein the audio representation may comprises direct positioning instructions of the region of interest, the X-ray source, and the X-ray detector. The audio guidance may comprise acoustic tones using the tone frequency and/or repetition intervals to indicate rotations or translations of the patient or the X-ray source or the X-ray detector.

According to an embodiment, determining the guidance data of the region of interest, the X-ray source and the X-ray detector may comprise a calculation of a pseudo X-ray image by utilizing the parametric 3D model. The pseudo X-ray image is a schematic representation of a projection that would result from a current alignment of the region of interest, the X-ray source and the X-ray detector. The pseudo X-ray image may be helpful to assess whether the current alignment is sufficient. This may be advantageous in terms of efficiency and quality.

A further aspect relates to a device for providing guidance data for positioning a region of interest of a subject, an X-ray source, and an X-ray detector. The device comprises: a processor configured, to obtain current positioning data of at least one palpable bony landmark of the region of interest from a measuring device, wherein the current positioning data is derived from a palpation of the at least one palpable bony landmark; the processor further configured, to obtain current positioning data of the X-ray source and of the X-ray detector; the processor further configured, to determine guidance data for positioning the region of interest, the X-ray source and the X-ray detector by utilizing a parametric 3D model and the obtained current positioning data of the at least one palpable bony landmark, of the X-ray source, and of the X-ray detector, the processor further configured, to provide the guidance data. The processor may be a CPU, a workstation, a controller, or a node of data center. The processor may be a single entity or may be distributed on a plurality of entities.

A further aspect relates to a system for medical imaging. The system comprises a device as described above and an X-ray system. The X-ray system comprises an X-ray source and an X-ray detector.

A last aspect relates to a computer program element, which when executed by a processor is configured to carry out the steps of the method described above. The processor may be part of the medical imaging system, or may be provided separately in another computer device. The computer program element might be stored on a computer unit, which might also be part of an embodiment. This computing unit may be configured to perform or induce performing of the steps of the method described above. Moreover, it may be configured to operate the components of the above-described device. The computing unit can be configured to operate automatically and/or to execute the orders of a user. A computer program may be loaded into a working memory of a data processor. The data processor may thus be equipped to carry out the method according to one of the preceding embodiments. This exemplary embodiment of the invention covers both, a computer program that right from the beginning uses the invention and computer program that by means of an update turns an existing program into a program that uses invention. Further, the computer program element might be able to provide all necessary steps to fulfill the procedure of an exemplary embodiment of the method as described above. According to a further exemplary embodiment of the present invention, a computer readable medium, such as a CD-ROM, USB stick or the like, is presented wherein the computer readable medium has a computer program element stored on it which computer program element is described by the preceding section. A computer program may be stored and/or distributed on a suitable medium, such as an optical storage medium or a solid state medium supplied together with or as part of other hardware, but may also be distributed in other forms, such as via the internet or other wired or wireless telecommunication systems. However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It is noted that the above embodiments may be combined with each other irrespective of the aspect involved. Accordingly, the method may be combined with structural features of the device and/or system of the other aspects and, likewise, the device and the system may be combined with features of each other, and may also be combined with features described above with regard to the method.

These and other aspects of the present invention will become apparent from and elucidated with reference to the embodiments described hereinafter.

BRIEF DESCRIPTION OF THE DRAWINGS

Exemplary embodiments of the invention will be described in the following drawings.

DETAILED DESCRIPTION OF EMBODIMENTS

Figure 1:
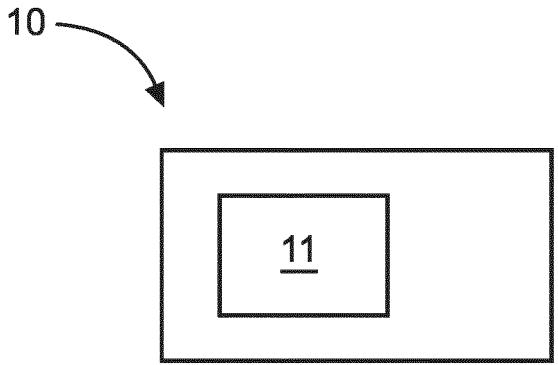
FIG. 1 shows a schematic view of a device according to a first embodiment of the present disclosure.

FIG. 1 shows a schematic view of a device 10 according to a first embodiment of the present disclosure. The device 10 is configured for providing guidance data for positioning a region of interest of a subject, an X-ray source, and an X-ray detector.

The device 10 comprises a processor 11, configured to obtain current positioning data of at least one palpable bony landmark of the region of interest from measuring device, wherein the current positioning data is derive from a palpation of the at least one palpable bony landmark. The processor 11 is in the present case a CPU of a workstation. The region of interest is, for example, a foot ankle and the at least one palpable bony landmark is a medial malleolus. The positioning data may be transmitted to the processor via a communication interface from the measuring device. The measuring device is in the present example a range camera, which can provide 3D positioning data. The processor 11 is further configured to obtain current positioning data of the X-ray source and of the X-ray detector. The positioning data of the X-ray source and the X-ray detector are in the present example also measured by the measuring device (i.e. range camera). Alternatively, the positioning data may be provided from a control of the X-ray system. The processor 11 is further configured, to determine guidance data for positioning the region of interest, the X-ray source and the X-ray detector by utilizing a parametric 3D model and the obtained current positioning data of the at least one palpable bony landmark, of the X-ray source, and of the X-ray detector. The parametric 3D model is in the present case stored on a storage medium of the device 10. Alternatively, the parametric 3D model could also be stored on a server of data center and there may be communication (e.g. Ethernet) between the processor and the server. The processor 11 is further configured, to provide the guidance data. The processor 11 has e.g, a communication interface, which is connected to a display configured to represent the guidance data.

Figure 2:
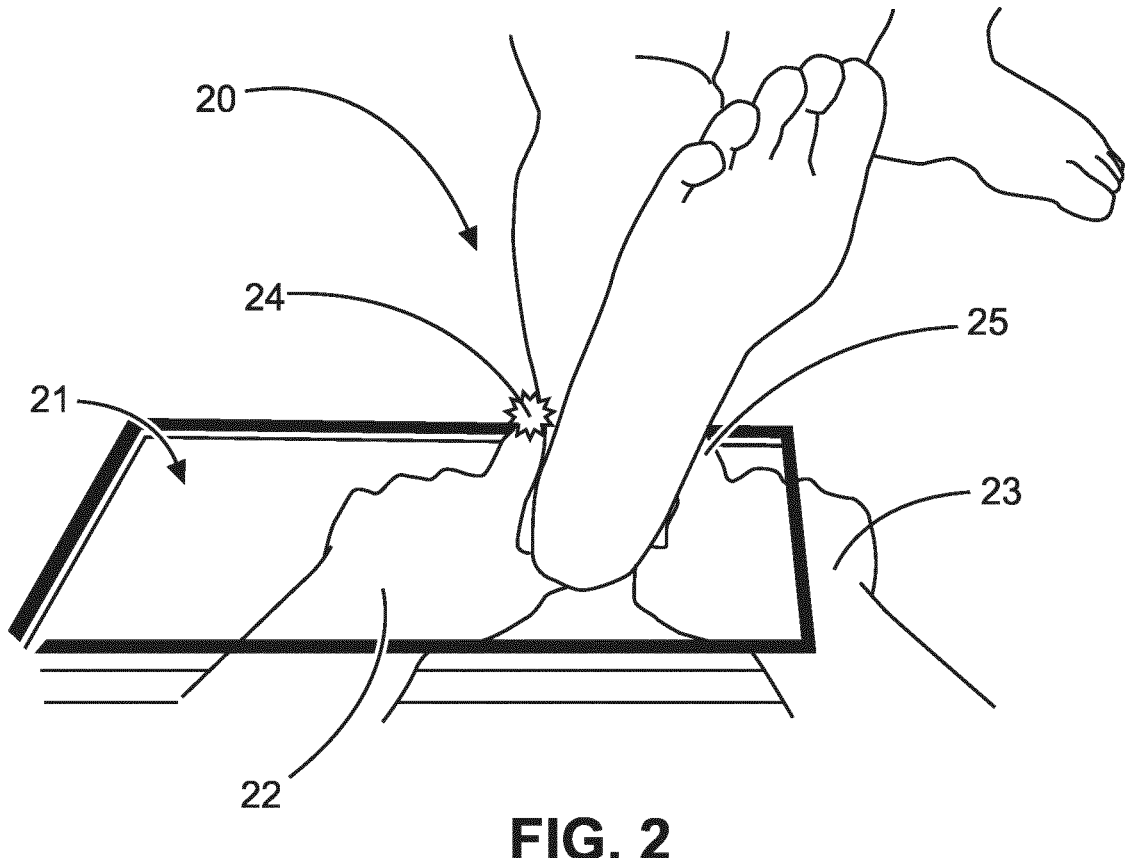
FIG. 2 shows a schematic diagram of a palpation of two palpable bony landmarks of a region of interest.

FIG. 2 shows a schematic diagram of a palpation of two palpable bony landmarks of a region of interest 20. The region of interest 20 is a foot ankle. The foot ankle is arranged on an X-ray detector 21, in the present case a digital cassette X-ray detector. A radiographer palpates with his hands 22 and 23 the region of interest 20. The radiographer palpates with a fingertip 24 of the left hand 22 the lateral malleolus and with a fingertip 25 of the right hand 23 the medial malleolus of the foot ankle. For example by means of speech recognition, the radiographer generates a trigger signal that triggers a measuring device (e.g. range camera not shown) to measure the spatial position of both fingertips 24 and 25 in order to obtain the positioning data of the palpable bony landmarks.

Figure 3:
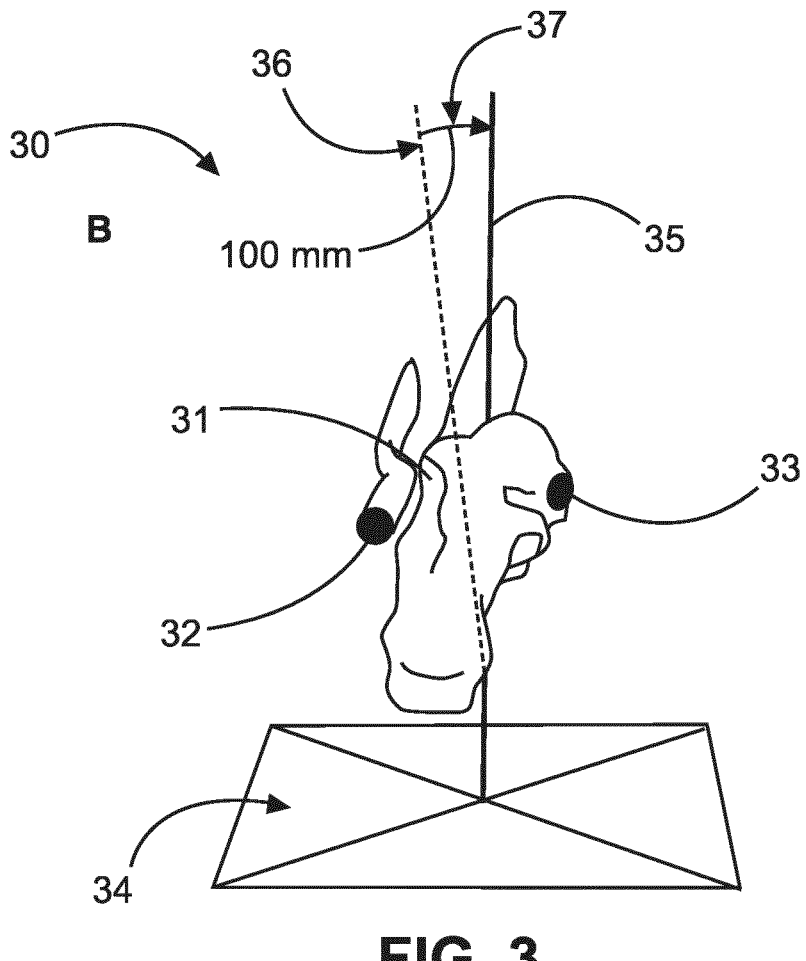
FIG. 3 shows a visual representation of guidance data.

FIG. 3 shows a visual representation of guidance data corresponding to the palpation shown in FIG. 2. The guidance data 30 is used for positioning the region of interest, the X-ray source, and the X-ray detector. The guidance data 30 shows a skeletal model of the foot ankle (i.e. region of interest 31) and the two palpated palpable bony landmarks 32 and 33. The guidance data 30 comprises a schematic representation of the ideal X-ray detector 34 and a central beam 35 of the X-ray source. The guidance data 30 further comprises a representation of the current central beam 36 and an arrow 37 with a displacement value, which guides the radiographer to adapt the X-ray source in this direction by 100 mm. The guidance data 30 aids in the present example the radiographer to adapt the position of the X-ray source and the X-ray detector. The guidance data is shown to the radiographer by means of augmented reality glasses. Alternatively, the guidance data is shown on a display in the examination room. The guidance data may further comprise different views of the region of interest.

Figure 4:
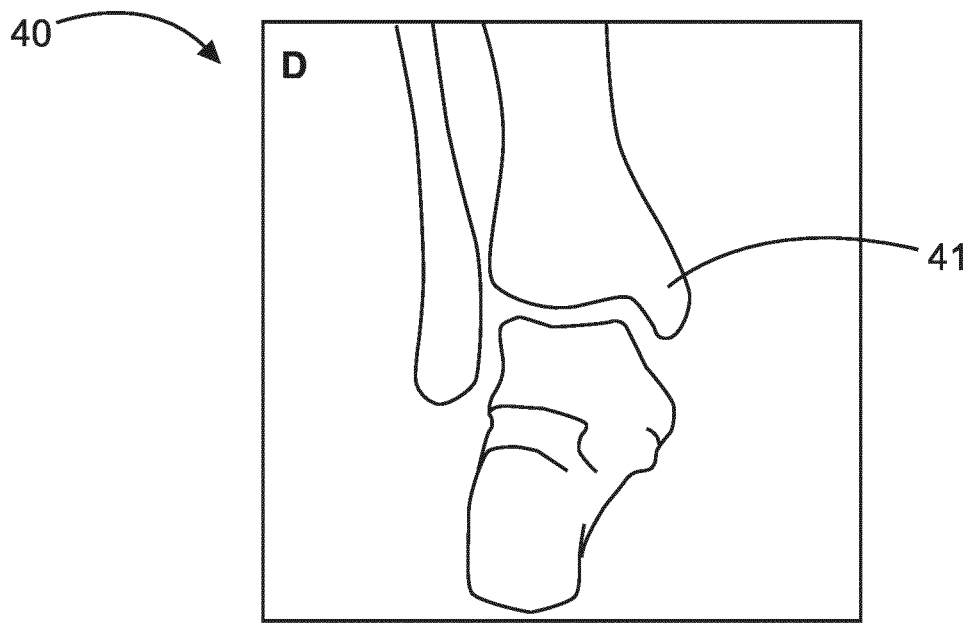
FIG. 4 shows a visual representation of guidance data according to a further embodiment.

FIG. 4 shows a visual representation of guidance data 40 according to a further embodiment. The guidance data 40 comprises a pseudo X-ray image of the region of interest 41, in the present example the foot ankle from FIG. 1. The pseudo X-ray image is calculated by utilizing the parametric 3D model. The pseudo X-ray image is a schematic representation of a projection that would result from a current alignment of the region of interest, the X-ray source and the X-ray detector. The pseudo X-ray image is presented to the radiographer by means of the augmented reality glasses.

Figure 5:
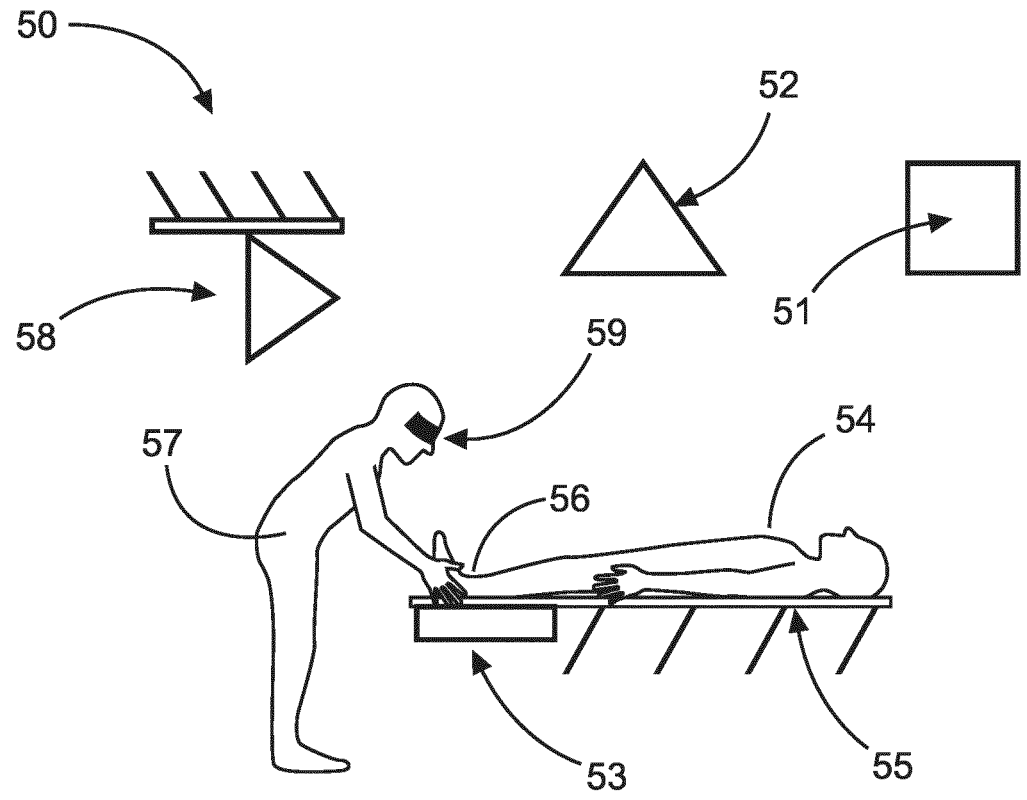
FIG. 5 shows a schematic view of a system according to an embodiment of the present disclosure.

FIG. 5 shows a schematic view of a system 50 for medical imaging. The system 50 comprises a device 51 for providing guidance data for positioning a region of interest of a subject, an X-ray source, an X-ray detector as described in FIG. 1. The system 50 comprises further an X-ray system, wherein the X-ray system comprises an X-ray source 52 and an X-ray detector 53. A subject 54 lies on a support 55. The region of interest 56 is a foot ankle, which is arranged above the X-ray detector 53, a digital cassette X-ray detector in the present example. Alternatively, any other X-ray detector could be used. A radiographer 57 carries out the preparation of the positioning of the region of interest 56, the X-ray source 52, and the X-ray detector 53. A measuring device 58 is arranged above the radiographer 57 and the region of interest 56 on a ceiling. The measuring device 58 is in the present example a RGB-D camera configured to measure the spatial position of the fingertips of radiographer palpating the region of interest. The measuring device 58 is further configured to measure positioning data of one or more anatomical landmarks of the region of interest such as the end of the foot and the knee joint. The measuring device 58 is further configured to measure the positioning data from the X-ray detector 53. In the present example, the position of the X-ray source is obtained by the control (not shown) of the X-ray system. The radiographer wears augmented reality glasses 59 configured to show the guidance data for positioning the region of interest, the X-ray source and the X-ray detector. The control of the X-ray system, the measuring device 58, the augmented reality glasses 59 and the device 51 are wireless connected by a WIFI, Bluetooth, or similar.

Figure 6:
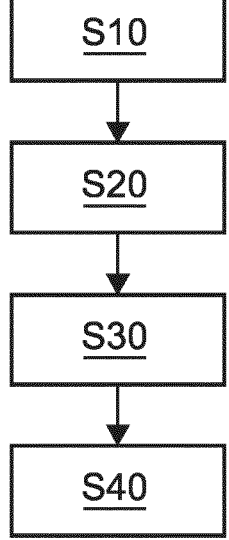
FIG. 6 shows a flow chart of a method according to an embodiment of the present disclosure.

FIG. 6 shows a flow chart of a method according to a further embodiment of the present disclosure. The method is used for providing guidance data for positioning a region of interest of a subject, an X-ray source and an X-ray detector. The method comprises the following steps. In step S10 by a processor current positioning data of at least one palpable bony landmark of the region of interest from a measuring device is obtained, wherein the current positioning data is derived from a palpation of the at least one palpable bony landmark. The current positioning data of the at least one palpable bony landmark may be obtained by measuring a spatial position of at least a fingertip of a radiographer or a soft tissue palpation robot palpating the at least one palpable bony landmark. The measuring of the spatial position of the least one fingertip may be initiated by a trigger signal configured to indicate that at least one fingertip of a radiographer or a soft tissue palpation robot palpates the at least one palpably bony landmark. The trigger signal may be generated actively by the radiographer and/or passively by a touch sensor arranged at the at least one fingertip of the radiographer or the soft tissue palpation robot. The trigger signal may be generated by a button pressed by the radiographer or by a pressure increase of the touch sensor. The spatial position of the fingertip may be measured with a range camera.

In step S20 current positioning data of the X-ray source and of the X-ray detector are obtained by the processor. The positioning data of the X-ray source and the X-ray detector may be measured with the range camera. Alternatively, the positioning data may be received from a control of the X-ray system or from another measuring device, e.g, a RGB-D camera. The measured positioning data are transmitted to the processor.

Step S30 comprises determining, by the processor, guidance data for positioning the region of interest, the X-ray source and the X-ray detector by utilizing a parametric 3D model and the obtained current positioning data of the at least one palpable bony landmark, of the X-ray source, and of the X-ray detector. The parametric 3D model may comprise anatomical parameters of the region of interest. The anatomical parameters may comprise at least one scale parameter of the region of interest and at least one degree of freedom of a movement of the region of interest. Optionally, by the processor, may further be received current positioning data of one or more anatomical landmarks of the region of interest, from the measuring device (e.g. range camera). Optionally, by the processor, may further be updated the parametric 3D model based on the received current positioning data of the one more anatomical landmarks of the region of interest. Optionally, by the processor, may further be determined a pose of the region of interest by utilizing the parametric 3D model and the obtained current positioning data of the at least one palpable bony landmark of the region of interest. Optionally by the processor may further be determined a comparison of the pose of the region of interest, the positioning data of the region of interest, the positioning data of the X-ray source and the X-ray detector with a target alignment of the region of interest, the X-ray source and the X-ray detector. The guidance data may be continuously determined. Optionally the guidance data may comprise a pseudo X-ray, wherein the pseudo X-ray image may be calculated by utilizing the parametric 3D model.

Step S40 comprises providing, by the processor, the guidance data. The guidance data may be provided by means of a visual representation and/or by means of audio representation. Optionally the guidance data may be provided continuously.

In another exemplary embodiment, a computer program or computer program element is provided that is characterized by being configured to execute the method steps of the method according to one of the preceding embodiments, on an appropriate system.

The computer program element might therefore be stored on a data processing unit, which might also be part of an embodiment. This data processing unit may be configured to perform or induce performing of the steps of the method described above. Moreover, it may be configured to operate the components of the above described device and/or system. The computing unit can be configured to operate automatically and/or to execute the orders of a user. A computer program may be loaded into a working memory of a data processor. The data processor may thus be equipped to carry out the method according to one of the preceding embodiments.

Further, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It is noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and the foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS 10, 51 device
11 processor
20, 31, 41, 56 region of interest
21, 34, 53 X-ray detector
22, 23 hand
24, 25 fingertip
30, 41 guidance data
32, 33 palpable bony landmarks
35 ideal central beam X-ray source
36 current central beam X-ray source
37 arrow
50 system
52 X-ray source
54 subject
55 support
57 radiographer
58 measuring device
59 augmented reality glasses
S10 obtaining current positioning data of palpable bony landmark
S20 obtaining current positioning data of X-ray source and X-ray detector
S30 determining guidance data
S40 providing guidance data

The invention claimed is:

1. A computer-implemented method for providing guidance data for positioning a region of interest of a subject, an X-ray source and an X-ray detector, comprising:
    obtaining current positioning data of at least one palpable bony landmark of the region of interest from a measuring device, wherein the current positioning data is derived from a palpation of the at least one palpable bony landmark;
    obtaining current positioning data of the X-ray source and of the X-ray detector;
    determining guidance data for positioning the region of interest, the X-ray source and the X-ray detector by utilizing i) a parametric 3D model configured to describe a pose of the region of interest and ii) the obtained current positioning data of the at least one palpable bony landmark, of the X-ray source, and of the X-ray detector; and
    providing the guidance data, wherein obtaining the current positioning data of the at least one palpable bony landmark of the region of interest comprises:
        measuring a spatial position of at least a fingertip of a soft tissue palpation robot palpating the least one palpable bony landmark, or
        indicating, via a trigger signal, that at least one fingertip of a soft tissue palpation robot palpates the at least one palpable bony landmark.

2. The method according to claim 1, wherein the trigger signal is generated actively by the radiographer and/or passively by a touch sensor arranged at the at least one fingertip of the soft tissue palpation robot.

3. The method according to claim 1, further comprising determining a pose of the region of interest by utilizing the parametric 3D model and the obtained current positioning data of the at least one palpable bony landmark of the region of interest.

4. The method according to claim 3, further comprising a comparison of the pose of the region of interest, the positioning data of the region of interest, the positioning data of the X-ray source and the X-ray detector with a target alignment of the region of interest, the X-ray source and the X-ray detector.

5. The method according to claim 1, wherein the parametric 3D model comprises anatomical parameters of the region of interest, and wherein the anatomical parameters comprise at least one scale parameter of the region of interest and at least one degree of freedom of a movement of the region of interest.

6. The method according to claim 1, further comprising:
    receiving current positioning data of one or more anatomical landmarks of the region of interest from the measuring device;
    updating the parametric 3D model based on the received current positioning data of the one or more anatomical landmarks of the region of interest.

7. The method according to claim 1, wherein the measuring device is an optical measuring device.

8. The method according to claim 1, wherein the guidance data are continuously determined and provided during positioning the region of interest of a subject, the X-ray source, and the X-ray detector.

9. The method according to claim 1, wherein providing the guidance data comprises a visual representation; and/or an audio representation.

10. The method according to claim 1, further comprising a calculation of a pseudo X-ray image by utilizing the parametric 3D model.

11. A device for providing guidance data for positioning a region of interest of a subject, an X-ray source, and an X-ray detector, comprising:
    a processor configured to:
        obtain current positioning data of at least one palpable bony landmark of the region of interest from a measuring device, wherein the current positioning data is derived from a palpation of the at least one palpable bony landmark;
        obtain current positioning data of the X-ray source and of the X-ray detector;
        determine guidance data for positioning the region of interest, the X-ray source and the X-ray detector by utilizing i) a parametric 3D model configured to describe a pose of the region of interest and ii) the obtained current positioning data of the at least one palpable bony landmark, of the X-ray source, and of the X-ray detector; and
    provide the guidance data, wherein obtaining the current positioning data of the at least one palpable bony landmark of the region of interest comprises:
        measuring a spatial position of at least a fingertip of a soft tissue palpation robot palpating the least one palpable bony landmark, or
        indicating, via a trigger signal, that at least one fingertip of a soft tissue palpation robot palpates the at least one palpable bony landmark.

12. A non-transitory computer-readable medium for storing executable instructions, which cause a method for providing guidance data for positioning a region of interest of a subject, an X-ray source and an X-ray detector, the method comprising:

obtaining current positioning data of at least one palpable bony landmark of the region of interest from a measuring device, wherein the current positioning data is derived from a palpation of the at least one palpable bony landmark;

obtaining current positioning data of the X-ray source and of the X-ray detector;

determining guidance data for positioning the region of interest, the X-ray source and the X-ray detector by i) utilizing a parametric 3D model configured to describe a pose of the region of interest and ii) the obtained current positioning data of the at least one palpable bony landmark, of the X-ray source, and of the X-ray detector; and providing the guidance data, wherein obtaining the current positioning data of the at least one palpable bony landmark of the region of interest comprises:

measuring a spatial position of at least a fingertip of a soft tissue palpation robot palpating the least one palpable bony landmark, or indicating, via a trigger signal, that at least one fingertip of a soft tissue palpation robot palpates the at least one palpable bony landmark.

* * * * *